United States Patent [19]

Beran

[11] 4,392,857
[45] Jul. 12, 1983

[54] TUBE HOLDER

[76] Inventor: Anthony V. Beran, 1472 La Loma Dr., Santa Ana, Calif. 92705

[21] Appl. No.: 256,698

[22] Filed: Apr. 23, 1981

[51] Int. Cl.³ .......................................... A61M 25/02
[52] U.S. Cl. .............................. 604/179; 128/207.17; 128/DIG. 26
[58] Field of Search ............................ 128/348–350 R, 128/207.17, DIG. 26; 24/16 PB, 30.5 P; 248/74 PB

[56] References Cited

U.S. PATENT DOCUMENTS

| 2,908,269 | 10/1959 | Cheng | 128/DIG. 26 |
| 3,339,246 | 9/1967 | Geisinger | 24/16 PB |
| 3,774,616 | 11/1973 | White et al. | 128/207.17 |
| 4,114,626 | 9/1978 | Beran | 128/348 |
| 4,249,529 | 2/1981 | Nestor et al. | 128/207.17 |

Primary Examiner—Dalton L. Truluck
Attorney, Agent, or Firm—Grover A. Frater

[57] ABSTRACT

A tube holder includes a clamp formed by a clamp base and a wrap-around strap. The strap is fixed at one end to the base and, after wrapping around the tube, is locked to the clamp base at a point along its length in a double locking system.

10 Claims, 7 Drawing Figures

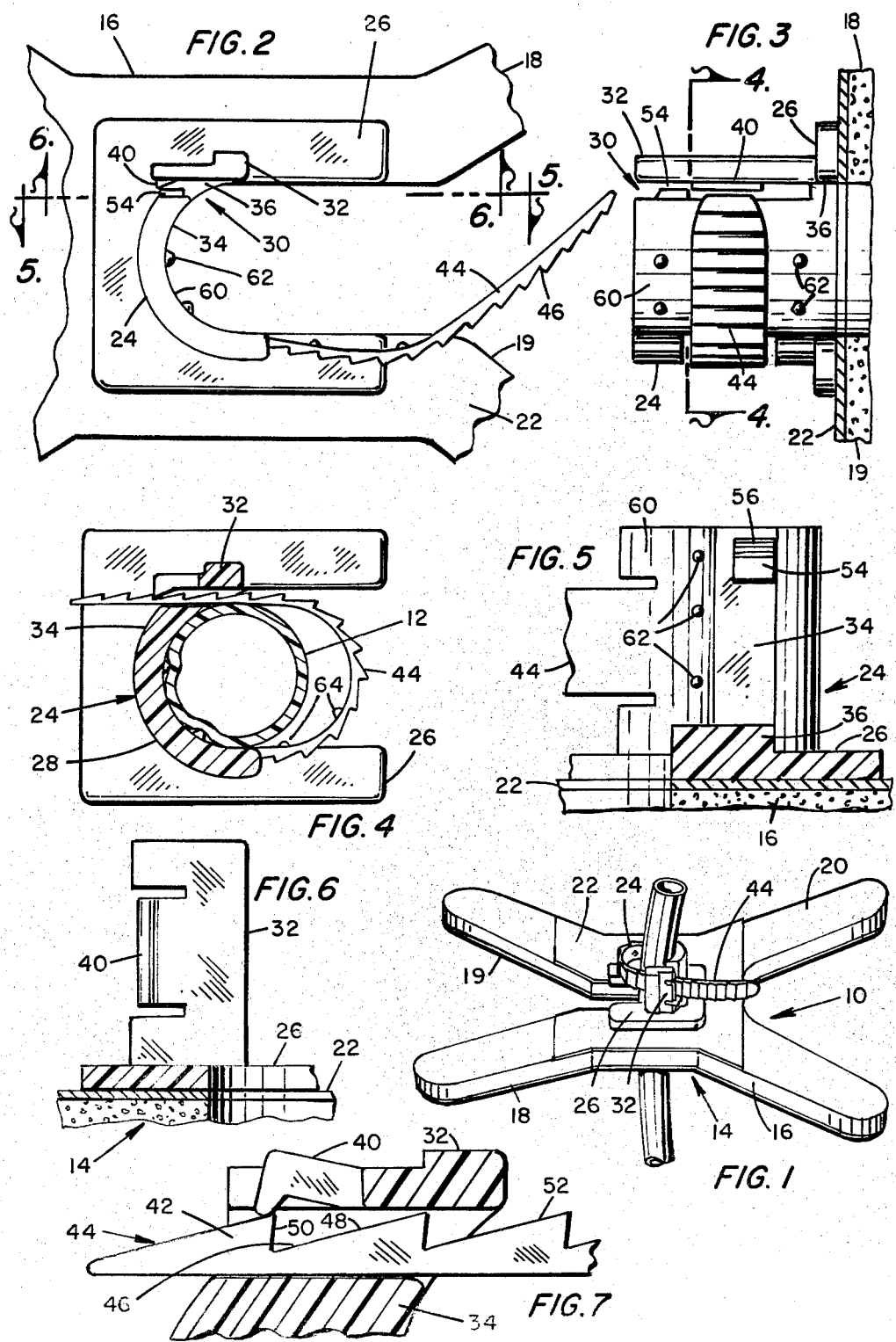

TUBE HOLDER

TECHNICAL FIELD

This invention relates to improvements in tube holders and particularly to clamping structures for tube holders.

BACKGROUND ART

While the invention has other applications, one of the most important is to hold endotracheal, gastrointestinal and other tubes and to fix their position relative to the patient in which such tubes are inserted. Those tubes enter at the patient's nostril or mouth and must be fixed to the patient to insure against unwanted change in the degree of insertion. If the patient is going to be able to move, the point of fixation must be right at the nose or mouth. Most of the practical holders include an adhesive patch to which a tube clamp is fixed.

A widely accepted and successful tube holder is shown in Beran U.S. Pat. No. 4,114,626. Its clamp is a two piece structure which is easily applied to, and readily removed from, patient and tube. It is intended primarily for use with infants—with small diameter tubes and a limited number of sizes. Each holder is designed for only one tube size.

The ideal tube holder for adult patients would be adjustable or otherwise arranged so that one holder would accommodate many tube sizes. The need for positive clamping is no less, and, indeed, is often greater in the case of adult patients because adult patients move more and they subject the tube and holder to greater forces than do infants. Another requirement for the adult tube holder is that it be easy for the medical technician and nurse to install and to remove, and difficult for the patient to remove. While difficulty of removal by a patient is not an often needed feature, it is important in certain cases. Thus, the ideal tube holder is one that exhibits that difference in ease of removal.

These holders include an adhesive surface and are used next to the patient's nose and mouth. Cleaning is not practical so the holder is a throw away product. The ideal holder is designed for production at very low cost, and presents minimum quality, storage, sterilization and packaging problems. The Beran holder of U.S. Pat. No. 4,114,626 meets these tests but, at least in adult sizes, the holder provided by this invention is best.

DISCLOSURE OF INVENTION

The invention provides a tube holder which is adjustable in that it can be used to hold tubes that have any of a number of different sizes. It provides a reliable, inexpensive, easily used holder, the holding action of which is positive. To provide a device with those characteristics is an object of the invention.

In the Beran two-piece locking system a locking cylinder is forced over a split cylinder which surrounds the tube. The mating surfaces of the locking cylinder and the holding cylinder are relatively tapered. The result is that the clamping action between tube and holder is applied over a relatively large area of the tube. The tapered shape provides a mechanical purchase that permits gripping of the tube with a larger force than is needed to press the locking and holding cylinders together.

The advantage of that system of force multiplication is lost when the two-piece design is replaced with a locking system which can be molded as a single unitary device. The invention overcomes that loss by a distortion of the cross-sectional shape of the tube. The holding structure is arranged so that the tube is pressed to slightly oval shape at the region at which it is engaged by the holder. That is augmented, or even replaced, by projections that extend from the holder into engagement with the exterior wall of the tube. In preferred form those projections do not pierce the tube wall but merely distort its shape in small degree.

The relatively tapered surfaces of the Beran two-piece holder engage one another over a large area such that friction alone provides adequate locking force. The one-piece arrangement or capability, in the invention, utilizes a different arrangement. One part of the holder cooperates with another part to embrace the tube, and the two parts are positively locked together. They are locked as bolt and latch. Matching conformations, one on one of the two parts and the other on the other part, serve one as the latch and the other as the bolt. The lock in the invention can be closed by either of two motions which differs in direction. The direction of one is perpendicular to the direction of the other. The conformation that is the latch in one locking motion is the engaged conformation in the other locking motion. In the preferred forms of the invention either motion, or both, is available to close the lock and hold the tube fast in the embrace of the two parts.

Adjustability is provided by a duplication of at least one of the two conformations at spaced points along a surface of that one of the two parts on which the conformation is formed. In preferred form one of the two parts is a strap and the conformation on the strap is reproduced at spaced points along its length. The strap serves as the bolt in a second lock.

In the second lock the bolt, or strap, is engaged in a keeper. In the preferred form of the invention the closure of the second lock is accomplished by either of the above described motions as the first lock is closed. The first lock prevents opening of the second in one of the two motion direction, and the second prevents opening of the first lock in the second of the two motion directions. Thus, a tube once locked in place can be released only by unlocking the second lock first whereupon the second lock can be unlocked.

A variety of structures may be employed in practice of the invention, and not all of its features are required to realize the advantages of the invention. In recognition that understanding is facilitated by examination of an example, description of some of the features of the invention has been transferred to a subsequent portion of this specification and to the claims. It is to be understood that the preferred embodiment depicted in the drawings and described below is but one example of the invention and that other embodiments of the invention are possible. Any application of the doctrine of equivalents is not to be restricted to the specific features of the preferred embodiment. The invention is defined in the appended claims.

BRIEF DESCRIPTION OF THE DRAWINGS

In the drawings:

FIG. 1 is an isometric showing of a holder, in which the invention is embodied, assembled with a tube, the holder clamp being shown as it appears during locking and unlocking of the clamp;

FIG. 2 is a top view of a fragment of the holder of FIG. 1;

FIG. 3 is a side view of the fragment of FIG. 2;

FIG. 4 is a sectional view taken on line 4—4 of FIG. 3 except that the end of the strap is shown to be inserted in the keeper and the tube wall deformed as if held tightly in the clamp;

FIGS. 5 and 6 are cross-sectional views taken on lines 5—5 and 6—6, respectively, of FIG. 2; and FIG. 7 is a fragmented, cross-sectional view looking down on the strap retainer structure and strap on a plane just above the upper edge of the strap and just below the double lock projection.

DESCRIPTION OF THE PREFERRED EMBODIMENT

The preferred embodiment of the invention includes most of its features. The specific form of those features have been selected as preferred for a nasal/oral tube application for the invention. The application has been selected on the basis of its importance. In other applications other specific forms might be considered preferable.

In FIG. 1 the holder 10 is shown assembled on a length of tubing 12. The tube is made of transparent plastic. It is resilient and relatively soft. It has a diameter which is within the range of tube diameters commonly used in intubating medical patients, and it is a commonly used type.

The holder 10 includes a patient attachment section 14 by which it is fixed to the face of the patient adjacent his mouth or nostril. Section 14 includes a central portion 16 from which four strap arms extend to form an X-shape. The strap arms are designated 18, 19, 20 and 21 for identification. The lower side of section 14, the side that is hidden from view in FIG. 1, is covered with a layer of pressure sensitive adhesive material by which section 14 is made to adhere to the patient's skin. A layer 22 of pressure adhesive tape material overlies central portion 16 of section 14 and is bonded to the pliant plastic foam material which forms the central portion 16 and the arms 18, 19, 20 and 21.

The upper portion 24 of the holder is the tube clamp section. It is joined, in this case it is formed integrally, with a flange 26 which is interposed between the clamp section 24 and the patient attachment section 14. The lower face of the flange 26 is bonded to the upper face of the tape material layer 22. The adhesive that joins the flange to layer 22 is strong. The margins of the flange need not extend much beyond the area occupied by the lower end of the clamp whereby the patient attachment portion is easily bent out of the plane of the flange close to the clamp section.

The clamp section includes a base which is slotted at one side from the end opposite the flange 26. The slot extends entirely through from one side of the base to the other in a plane perpendicular to the plane of the flange. The slot is almost as deep as the base is high. Thus, the base can be considered as consisting of the semi-circular segment 28 at one side of the slot 30 (FIGS. 2 and 3) and the latch post 32. Alternatively, the latch post 32 and the opposing structure 34 can be thought of as arms of a U-shaped member connected by connecting section 36. One arm, arm 34 in this case, is then integrally formed with the base 24.

A latch 40 is fixed to the latch post 32 such that it extends into the slot 30. It need not actually be in the slot but could be positioned beyond the slot itself. Its position lengthwise of the slot is less important than that its normal, relaxed position is in the plane of the slot. In this embodiment the latch is about one-third or one-half as wide as the slot is deep and it is positioned in the midregion of the slot's depth.

The post 32 is formed of resilient material. It can be bent away from the base 24, and more particularly from "arm" 34 to widen the slot 30. The latch 40 is formed integrally with post 32. Spaced slots in the latch post define the latch as a cantilever the end of which is formed as a triangular prism. It is the triangular part that extends into the plane of the slot. Being formed of resilient material, it can be cantilevered back out of that plane as it is shown to be in FIG. 7 by the portion 42 of strap 44.

The strap can be considered to be a bolt which can be moved in the direction of its length through the slot, to the left in FIGS. 1, 4 and 7 of the drawing. The conformation 46 on the strap is a triangular slot into which the latch 40 will spring if the strap 44 is moved leftward in FIG. 7 to bring the conformation 46 into position opposite to triangular portion of the latch. Conformation 46 is formed by a sloping surface 48 and a near perpendicular surface 50. It will be apparent that the strap can be moved to the left in FIG. 7. The latch will be cammed back by the sloping surface 46 and 52 of the next conformation. However, once the strap has been inserted to a degree that permits entry of the latch into a notch of the strap, the strap is locked against withdrawal by rightward movement.

These two conformations, the triangular projection of the latch and the triangular notch of the strap, constitute the first lock in this embodiment. The position of the conformations can be reversed and their shape can be other than triangular, and other variations are possible. However, it is a feature that the two conformations can be interlocked either by movement of the strap through the slot from one side toward the other or by matching the conformations by movement of the strap while positioned above the latch and then moving the strap down into the slot until the conformations interlock or mesh.

Such downward motion is impeded by a projection which extends into the slot above the latch from one or the other side of the slot. It is preferred that the projection extend from arm 34 opposite the latch post arm 32. It is numbered 54 in the drawings. The upper surface 56 slopes downwardly into the slot but the lower surface is perpendicular to the plane of the slot. The projection is positioned above the latch 40. It does not interfere with insertion of the end of the strap into the slot or with movement of the strap through the slot in the direction of the length of the strap. However, the projection does interfere with movement of the strap vertically in and out of the slot from and to the open end of the slot. Motion of the strap into the slot past the projection is possible because of the sloping upper surface and the resilience of the latch post. The side of the strap being forced down against the sloping surface, the strap will be cammed against the latch post. The post will be forced away from the projection until the strap can slide down past the projection. If a strap notch is aligned with the latch the strap continues down. If not aligned the strap is pushed through the slot until there is alignment.

Removal of the strap upwardly in the slot past the projection is another matter. The projection's lower face is perpendicular. The strap is locked in place by the lower face as a second lock. It can be removed only by widening the slot, in this embodiment by bending the latch post. That can be done by pulling the post with one finger while lifting the strap with another or by forcing the end of the strap against the post and upwardly simultaneously to bend the post and force the strap clear of the latch and projection.

In the preferred embodiment the semi-circular part 28 of the base is only approximately semi-circular. The other end of the strap 44 is fixed to the part 28 at the side opposite the U-shaped strap keeper. It must be, and is, flexible and it exhibits some resilience. In the preferred embodiment it is molded integrally with the remainder of the tube clamp section and along with latch post 24 forms a part of that section. In the preferred embodiment the strap is molded such that it occupies substantially the position shown in FIGS. 2 and 3 of the drawing. The end extends away from the base generally parallel at first with the plane of the slot, and then it curves inwardly toward the plane of the slot. As best shown in FIGS. 2 and 3 the strap is relatively wide and the triangularly shaped conformation 46 is repeated at spaced points along substantially all of its length. It lies in a plane that is parallel with the plane of the base 26. Those conformations extend entirely across the width of the strap and are parallel to the side walls of the slot and to the inner surface 60 of the semi-circular base 28.

Surface 60 extends lengthwise over the length of the base. As best shown in FIG. 1, the patient attachment section 14 and the flange 26 are cut away from the region which is faced by surface 60. While the end of the strap 44 extends into that region, the way is clear to move a section along the length of a tube between arms 18 and 19 past the end of the strap 44 and against surface 60. To clamp it in place the free end of strap 44 is wrapped around to the region of the latch post 32. The end of the strap may be inserted into the slot 30 below projection 54 and then pushed through the slot, ratcheting the latch until the strap embraces the tube 12 tightly enough to cause deformation of the tube wall by the several small projections 62 which extend from surface 60. The deformation is depicted in FIG. 4. In that figure the strap is not drawn into tight embrace around the tube 12 but the normally circular tube wall is shown to be deformed by the projections on wall 60 as it would be if the strap was tight. Additional projections 64 are formed on the side of the strap toward the tube and they, too, cause a slight deformation of the tube wall when the strap is drawn tight.

It is not necessary to "thread" the end of the strap into the slot 30 from the side. It is more convenient to lift the end of the strap around the tube and over the slot. The edge of the strap is easily directed into the slot as it is shown to be in FIG. 1. Pressing down gently but firmly at the side of the strap beyond the latch post forces the strap to cam the post away from projection 54 and down to the latch. Matching the latch and a groove of the strap is easily accomplished with a minimum of finger manipulation. When the conformations are aligned the strap is forced down past the projection 54. FIG. 4 represents the condition at that point in the process. The strap is locked in the strap retainer so that it cannot be withdrawn from the side or the end of slot 30. However, the strap can be forced farther through the slot by ratcheting past the latch 40 until the strap is tight against the tube 12 and the tube wall is deformed by both sets, 62 and 64, of projection.

The holder can be attached to the patient before or after assembly of the tube with the clamp and clamping can be completed at any point in the process.

When the clamp is to be opened, either for removal or adjustment of degree of tube insertion, the end of the strap 44 is lifted up to separate the latch and strap conformations, as shown in FIG. 1. To do that the slot must be opened to permit the strap to slide between the projection 54 and post 32. Fingernail pressure on the post, or applying outward and upward force on the end of the strap, will provide the required slot opening.

While the double locking arrangement seems complex in the abstract, it is convenient to use, and it can be accomplished in a relatively simple, easily manufactured, reliable structure. This preferred embodiment is an example.

I claim:

1. A tube clamp comprising:
    a clamp base including a lengthwise surface adapted to lie disposed against a section of the length of a tube;
    a U-shaped strap retainer fixed to the base at one side of said lengthwise surface, the arms of the U-shape extending substantially parallel said surface;
    a strap fixed at one end to said base at the other side of said lengthwise surface;
    complementally formed conformations on at least one side of said strap and one arm of said U-shaped strap retainer, the separation of said arms being such that said strap may be inserted sidewise between the arms of the strap retainer when said conformations are aligned and may not be inserted endwise between the arms without retraction of one of said conformations;
    the width of said strap being less than the length of at least one of said arms of the U-shaped strap retainer; and
    a projection extending from one arm toward the other of said U-shaped strap retainer at a point near the upper end of said one arm, the degree of extension being such as to preclude sidewise insertion of the strap between said arms, and sidewise removal, unless the arms of the U-shaped strap retainer are separated beyond their separation in relaxed condition.

2. The invention defined in claim 1 in which said conformation on the strap is repeated at spaced intervals along the length of the strap.

3. The invention defined in claim 2 in which the conformation on said arm is resiliently mounted thereon such that it is forced toward retracted position as an incident to insertion of the strap into the space between the arms of the U-shaped member except when opposite one of the conformations on the strap.

4. The invention defined in claim 3 in which said conformations of the strap have saw-tooth shape, the sloping portion of each conformation extending to greater strap thickness in the direction away from the free end of said strap whereby the conformation of the arm is cammed to retracted position at successive conformations of the strap as the strap is urged in the direction of its length through the space between said arms.

5. The invention defined in claim 3 in which said U-shaped strap retainer is integrally formed with said clamp base at one of its arms.

6. The invention defined in claim 5 in which the strap retainer is integrally formed with said clamp base at that one of the strap retainer arms on which said projection is formed.

7. The invention defined in claim 1 which further comprises means in the form of projections extending from said lengthwise surface for rotational and lengthwise movement relative to said surface of a tube when held to said surface by said strap.

8. The invention defined in claim 1 which further comprises an adhesive patch fixed to said clamp base at the end thereof opposite the end to which said U-shaped strap retainer opens, the patch having shape to permit placement of a tube which extends on opposite sides of said patch against said lengthwise surface.

9. The invention defined in claim 8 in which said patch is X-shaped and is attached to said clamp base at the junction of the arms of the X-shape.

10. A tube clamp comprising:
   a clamp base having a lengthwise surface adapted to lie against a section of the length of a tube;
   said base being formed with a through slot adjacent to said surface and the end of said slot opening toward one end of the base along the length of said surface;
   a strap carried by said base at the side of said lengthwise surface opposite said slot, the width of the strap lying parallel to the plane of the slot;
   a complementally formed groove and rib, one on the strap and the other on a surface of the base in the region of the slot and both extending parallel to the width of the strap, the rib being resiliently mounted for movement in the direction across the slot; and
   a projection formed on one wall of said slot adjacent to said slot opening and extending in a direction across the width of said slot such that the width of the slot at said projection is less than the width of the strap and its conformation, the strap and its conformation having width to permit insertion of the strap endwise from the side of the slot and edgewise into the slot from the end of the slot when said conformations are aligned and only when the walls of the base that form the slot are spread apart at said projection sufficiently to accommodate the width of the strap and its conformation.

* * * * *